US00PP17733P2

(12) United States Plant Patent
Dekker

(10) Patent No.: US PP17,733 P2
(45) Date of Patent: May 15, 2007

(54) ***CHRYSANTHEMUM* PLANT NAMED 'EUROBELLE LEMON'**

(50) Latin Name: *Chrysanthemum×morifolium*
Varietal Denomination: Eurobelle Lemon

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 11/267,869

(22) Filed: Nov. 4, 2005

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Eurobelle Lemon', characterized by its decorative-type inflorescences with ovate-shaped, light yellow-colored ray florets; strong and upright flowering stems; freely flowering habit; early and uniform flowering response; and good postproduction longevity.

2 Drawing Sheets

Botanical designation: *Chrysanthemum×morifolium.*
Cultivar denomination: 'Eurobelle Lemon'.

BACKGROUND OF THE INVENTION

The present invention relates to a new and distinct cultivar of *Chrysanthemum* plant, botanically known as *Chrysanthemum×morifolium* and referred to by the name 'Eurobelle Lemon'.

The new *Chrysanthemum* is a naturally-occurring whole plant mutation of the *Chrysanthemum×morifolium* cultivar Eurobelle Yellow, not patented. The new *Chrysanthemum* was discovered and selected by the Inventor in January, 2004 as a single flowering plant within a population of plants of the cultivar Eurobelle Yellow in a controlled environment in Hensbroek, The Netherlands.

Asexual reproduction of the new *Chrysanthemum* by terminal cuttings harvested in Hensbroek, The Netherlands since February, 2004, has shown that the unique features of this new *Chrysanthemum* are stable and reproduced true to type in successive generations.

BRIEF SUMMARY OF THE INVENTION

The cultivar Eurobelle Lemon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Eurobelle Lemon'. These characteristics in combination distinguish 'Eurobelle Lemon' as a new and distinct cultivar:

1. Decorative-type inflorescences with ovate-shaped, light yellow-colored ray florets; typically grown as a spray-type.
2. Strong and upright flowering stems.
3. Freely flowering habit.
4. Early and uniform flowering response.
5. Good postproduction longevity.

Plants of the new *Chrysanthemum* can be compared to plants of the parent, the cultivar Eurobelle Yellow. In side-by-side comparisons conducted in Hensbroek, The Netherlands, plants of the new *Chrysanthemum* differed from plants of the cultivar Eurobelle Yellow primarily in ray floret coloration as plants of the new *Chrysanthemum* have darker yellow-colored ray florets.

Plants of the new *Chrysanthemum* can be compared to plants of the *Chrysanthemum* cultivar Eurobelle, disclosed in U.S. Plant Pat. No. 12,659. In side-by-side comparisons conducted in Hensbroek, The Netherlands, plants of the new *Chrysanthemum* differed primarily from plants of the cultivar Eurobelle in the following characteristics:

1. Plants of the new *Chrysanthemum* had more ray florets per inflorescence than plants of the cultivar Eurobelle.
2. Ray florets of plants of the new *Chrysanthemum* and the cultivar Eurobelle differed in color as ray florets of plants of the cultivar Eurobelle were white in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph on the first sheet comprises a side perspective view of a typical flowering stem of 'Eurobelle Lemon'.

The photograph at the top of the second sheet comprises a close-up view of typical inflorescences of 'Eurobelle Lemon'.

The photograph at the bottom of the second sheet is a close-up view of the upper and lower surfaces of typical inflorescences and leaves of 'Eurobelle Lemon'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about nine weeks from planting when the photographs and the description were taken.

Botanical classification: *Chrysanthemum×morifolium* cultivar Eurobelle Lemon.

Commercial classification: Decorative-type *Chrysanthemum* typically grown as a spray-type cut flower.

Parentage: Naturally-occurring whole plant mutation of the *Chrysanthemum×morifolium* Eurobelle Yellow, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative-type cut *Chrysanthemum;* typically grown as a spray-type; erect and strong flowering stems. Vigorous growth habit.

*Flowering stem description.*—Length: About 70 cm to 80 cm. Diameter: About 6 mm. Strength: Strong. Texture: Pubescent. Aspect: Erect. Branching habit: Plants are typically grown as single stems. Color: Close to 146B.

*Foliage description.*—Arrangement: Alternate. Length: About 7 cm to 16 cm. Width: About 4 cm to 8 cm. Apex: Cuspidate. Base: Attenuate. Margin: Palmately lobed. Texture, upper and lower surface: Pubescent; rough. Petiole length: About 5 mm to 3 cm. Color: Developing foliage, upper surface: Darker than 137A. Developing foliage, lower surface: 137B to 137C. Fully expanded foliage, upper surface: 137A; venation, 147B. Fully expanded foliage, lower surface: Close to 147B; venation, 147C. Petiole, upper and lower surfaces: 147B.

Inflorescence description:

*Appearance.*—Decorative-type inflorescence form with ovate-shaped ray florets. Inflorescences borne on terminals above foliage. Disk and ray florets develop acropetally on a capitulum. Inflorescences not fragrant. Typically grown as spray-types.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about three weeks.

*Quantity of inflorescences per flowering stem.*—About 13 to 18 inflorescences per flowering stem.

*Inflorescence size.*—Diameter: About 5 cm to 7 cm. Depth (height): About 2 cm to 2.5 cm. Diameter of disc: About 6 mm.

*Inflorescence buds.*—Height: About 6 mm to 8 mm. Diameter: About 8 mm to 1 cm. Shape: Spherical. Color: 137A.

*Ray florets.*—Length: About 1.2 cm to 3.5 cm. Width: About 1 cm to1.3 cm. Shape: Ovate. Apex: Praemorse. Base: Attenuate; fused. Margin: Entire. Texture, upper and lower surfaces: Smooth, glabrous. Number of ray florets per inflorescence: About 220 in numerous whorls. Color: When opening, upper surface: 4C. When opening, lower surface: 4D. Fully opened, upper surface: 4C to 4D. Fully opened, lower surface: 155C.

*Disc florets.*—Shape: Tubular; elongated. Length: About 5 mm. Width: About 1 mm. Number of disc florets per inflorescence: About ten. Color: Immature: 145A to 145B. Mature: Apex: 145A. Midsection: 21C. Base: 145D.

*Peduncles.*—Length, terminal peduncle: About 8 cm. Length, fourth peduncle: About 13 cm. Diameter: About 2 mm to 3 mm. Angle: About 60° from vertical. Strength: Strong. Texture: Pubescent. Color: 137C.

*Reproductive organs.*—Androecium: None observed on disc florets. Gynoecium: None observed on ray or disc florets.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Eurobelle Lemon', as illustrated and described.

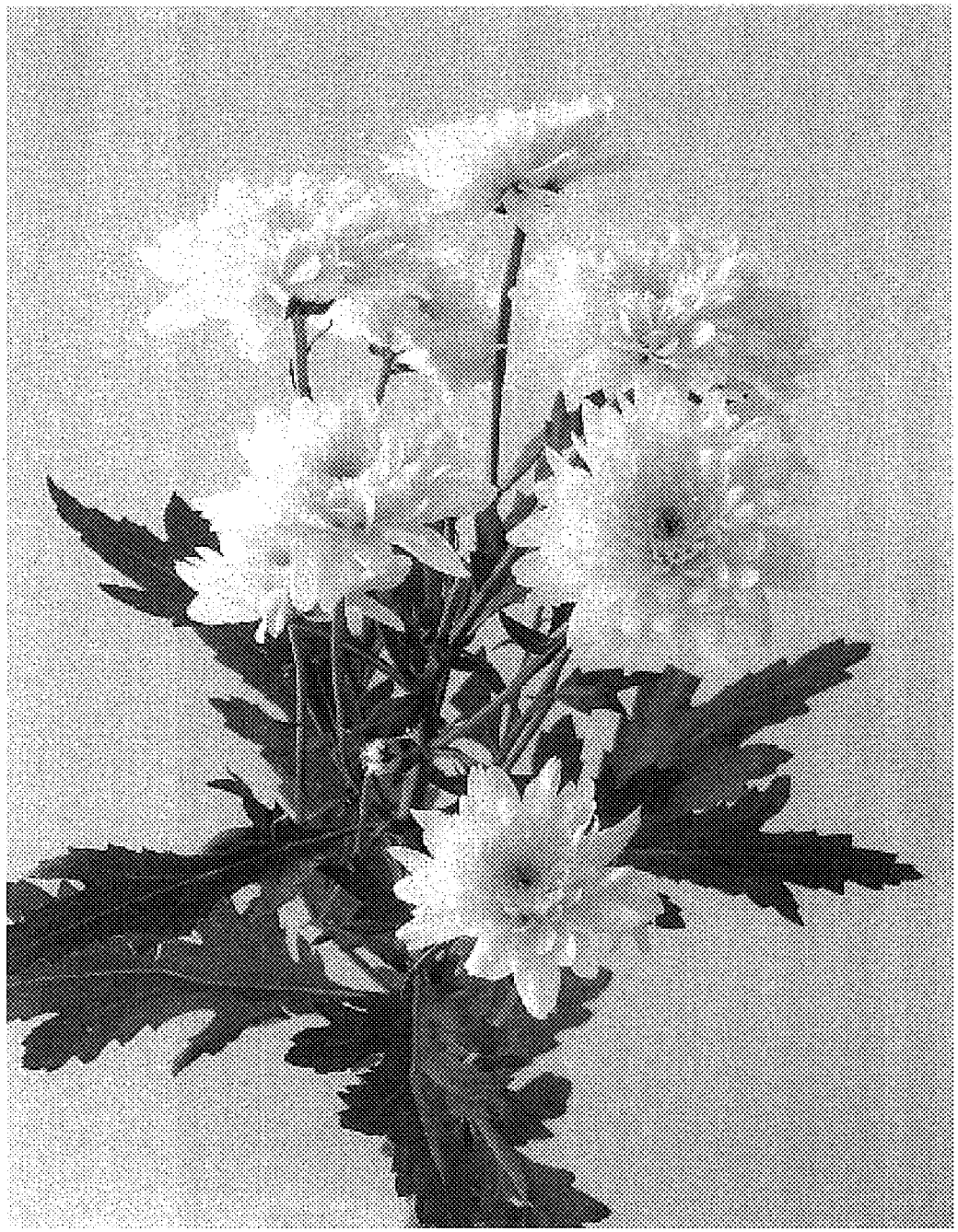

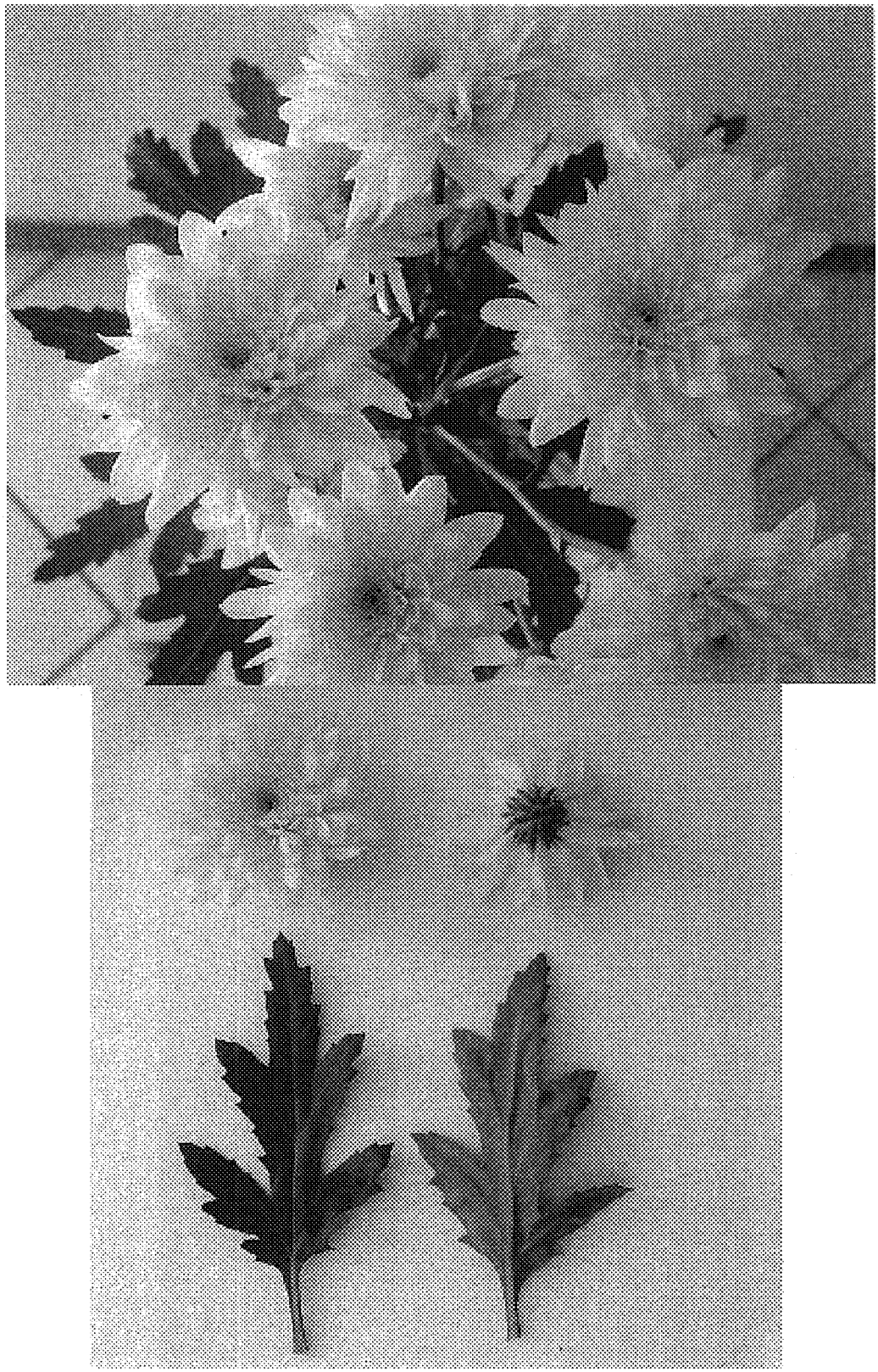

* * * * *